United States Patent [19]

Wan

[11] Patent Number: 4,647,657

[45] Date of Patent: Mar. 3, 1987

[54] HETEROPOLYSACCHARIDE - NW-01

[75] Inventor: Chiu-Chi Wan, Fishkill, N.Y.

[73] Assignee: Texaco Inc., White Plains, N.Y.

[21] Appl. No.: 775,087

[22] Filed: Sep. 12, 1985

[51] Int. Cl.$^4$ ............................................. C08B 37/00
[52] U.S. Cl. ..................................... 536/123; 536/1.1; 536/114
[58] Field of Search .......................... 536/123, 114, 1.1

[56] References Cited

U.S. PATENT DOCUMENTS 4,304,906 12/1981 Kang et al. .......................... 536/114
4,536,496 8/1985 Shimizu et al. ...................... 536/123

Primary Examiner—Johnnie R. Brown
Attorney, Agent, or Firm—Robert A. Kulason; James J. O'Loughlin

[57] ABSTRACT

The new heteropolysaccharide NW-01 prepared by the fermentation of a Flavobacterium species ATCC 53201 has valuable properties as a viscosity and mobility control agent in aqueous systems and useful in preparing oil well drilling fluids. Its chemical composition consists of glucose, arabinose and galactose in a 4.8:3.3:1 molar ratio.

1 Claim, No Drawings

HETEROPOLYSACCHARIDE - NW-01

BACKGROUND OF THE INVENTION

Compound NW-01 may be prepared by fermentation in a suitable nutrient medium with a hitherto undescribed organism which, based on studies, is Flavobacterium species. A permanent deposit of this organism employed in making the heteropolysaccharide of the invention was made with the American Type Culture Collection on July 31, 1985 under Accession Number ATCC 53201.

DESCRIPTION OF THE STRAIN

Characteristics of Colonial Morphology

On YM (yeast-malt) agar, the bacterial typically grow to colonies of about 3 millimeters in diameter in 72 hours. The organism form circular, convex, entire, smooth, opaque yellow-colored colonies. The colonies are heavily mucoid but lose their shininess and become waxy after four to five days.

Characteristics of Cell Morphology

Strain NW-01 is a gram-negative, non-motile, thick rod-shaped bacterium. On nutrient agar, the average size of the cell is about 0.78 by 1.8 microns. The organism usually occurs as single cells and only rarely form chains. The bacterium was found to be non-fermentative.

TABLE I

Biochemical and Other Tests Employed for the Strain NW-01

| Test | Result | Fermentation of O-F Medium: | |
|---|---|---|---|
| Growth at 4° C. | + | | |
| 25° C. | + | | |
| 30° C. | + | L-arabinose | + |
| 37° C. | − | Cellobiose | + |
| Growth at pH 6.0 | + | Ethanol | K |
| Growth with 3% NaCl | − | D-fructose | + |
| Growth with 6.5% NaCl | − | D-glucose (open) | + |
| MacConkey agar growth | − | D-glucose (closed) | − |
| Skim milk agar growth | + | Glycerol | + |
| Aesculin hydrolysis | − | I—inositol | K |
| Casein hydrolysis | − | Lactose | K |
| Starch hydrolysis | − | Maltose | + |
| Gelatinase | − | D-mannitol | K |
| Tween 20 hydrolysis | + | D-mannose | + |
| Tween 80 hydrolysis | + | L-rhamnose | K |
| Indole | − | D-ribose | + |
| Simmons citrate growth | + | Sucrose | + |
| Urease | − | Trehalose | + |
| Nitrate to nitrite | − | D-xylose | + |
| Nitrite reduction | − | Adonitol | K |
| Nitrite to nitrogen gas | − | Dulcitol | K |
| Hydrogen sulfide (TSI) | − | D-galactose | + |
| Lysine decarboxylase | − | Inulin | K |
| Arginine (Mollers) | − | Salicin | K |
| Ornithine decarboxylase | − | D-sorbitol | K |
| Phenylalanine deamination | + | Control | K |
| Lecithinase | − | | |
| Phosphatase | − | | |
| Catalase | + | | |
| Oxidase | + | | |
| Gluconate oxidation | N.G. | | |
| Growth on malonate as sole carbon source | − | | |
| Tyrosine degradation | − | | |
| dl-hydroxybutyrate growth | + | | |
| PHB accumulation | − | | |
| Deoxyribonuclease | + | | |
| Growth on 0.05% cetrimide | − | | |
| Growth on acetate as sole carbon source | + | | |
| Testosterone degradation | − | | |
| 1% NaCl growth | W | | |

TABLE I-continued

| | |
|---|---|
| Mucoid growth on glucose agar | + |
| 0.1% TTC growth | − |
| 0.02% TTC growth | + |

| Sole Carbon Sources: | |
|---|---|
| L-arabinose | + |
| Cellobiose | + |
| D-fructose | − |
| D-glucose | + |
| Lactose | + |
| Maltose | + |
| D-mannitol | + |
| L-rhamnose | − |
| D-ribose | − |
| D-sorbitol | − |
| Sucrose | − |
| Trehalose | + |
| D-xylose | + |
| Adonitol | + |
| Erythritol | − |
| Glycerol | + |
| Ethanol | − |
| Geraniol | − |
| I—inositol | − |
| Sebacic acid | − |
| Acetamide | + |
| Adipate | − |
| Benzoate | − |
| Butyrate | − |
| Citraconate | − |
| D-gluconate | + |
| M-hydroxybenzoate | − |
| 2-Ketogluconate | + |
| DL-lactate | − |
| L-malate | + |
| Pelargonate | − |
| Propionate | + |
| Quinate | + |
| Succinate | + |
| L-+-tartrate | − |
| Valerate | − |
| B—alanine | − |
| D-A-alanine | + |
| Betaine | − |
| Glycine | − |
| L-histidine | − |
| DL-norleucine | − |
| L-proline | + |
| D-tryptophan | − |
| L-valine | − |
| DL-arginine | − |
| Benzylamine | − |
| Butylamine | − |
| Putrescine | − |
| Mesoconate | − |
| DL-glycerate | − |
| L-tryptophan | − |

Bacterial Characterization

The isolate submitted as NW-01 has been characterized and is best described as Flavobacterium sp. Here is a comparison of characteristics of the genus Flavobacterium with those of the NW-01 strain.

| | Flavobacterium | NW-01 strain |
|---|---|---|
| PHB inclusions | − | − |
| Non-motile | + | + |
| Respiratory Metabolism | + | + |
| Growth at 5° C.-30° C. | + | + |
| Pigment yellow to orange | + | + |
| Catalase | + | + |
| Oxidase | + | + |
| Casein Hydrolysis | ± | − |
| Gelatin Hydrolysis | ± | − |
| Nitrate reduction | ± | − |
| DNAse | + | + |
| Aesculin | ± | − |
| Carbohydrate Fermentation: | | |
| Adonitol | − | − |
| Dulcitol | − | − |
| Fructose | + | + |
| Glucose | + | + |

TABLE I-continued

| | | |
|---|---|---|
| Glycerol | + | + |
| Inositol | − | − |
| Maltose | + | + |
| Sorbitol | − | − |
| Trehalose | + | + |

W = weak
+ = acid
K = alkaline
− = no change
N.G. = no growth
TTC = Triphenyl-tetrazolium chloride The novel bacterium of the invention was isolated from waste water, a sample of which was streaked onto YM (yeast-malt) agar plates. The YM agar was formed by adding to 1000 ml of distilled water 41 grams of a commercial mixture containing 3 parts by weight of a yeast extract, 3 parts by weight of a malt extract, 5 parts by weight of a peptone, and 10 parts by weight of dextrose together with 20 parts by weight of agar. The YM agar plates were incubated at 30° C. for 48–72 hours. After incubation, the plates were examined and the slimy colonies were transferred to fresh YM agar plates for further incubation. The cultures were purified by subculturing onto YM agar plates. The purified cultures were finally transferred onto YM slants and maintained in the lyophilized state.

In practicing our invention, a suitable nutrient fermentation medium, preferably corn steep liquor (CSL, 2.5 percent glucose, 0.4 percent corn steep liquor, 0.5 percent $K_2HPO_4$, 0.01 percent $MgSO_4$, pH=6.8–7.0) is inoculated with a culture of Flavobacterium species and permitted to incubate at a temperature of about 26° C. to 30° C., preferably 28° C., for a period of about 170 to 190 hours. Maximum heteropolysaccharide is produced in CSL medium when the glucose concentration is around 2.3–2.7 percent (W/V) and preferably 2.5 percent. Starch is also efficiently utilized by the culture and a comparable yield of the polysaccharide is produced therefrom.

The optimum pH for production of the heteropolysaccharide NW-01 is in the range of about 6.5–7.5, preferably about 7.0. Control of the pH can generally be obtained by the use of a buffer compound such as di-potassium acid phosphate at a concentration from about 0.4 to about 0.6 percent by weight of the fermentation medium. Potassium salts of phosphoric acid, for example, potassium di-hydrogen phosphate and potassium hydrogen phosphate, may be used as buffers. The pH can also be controlled by using a pH controller coupled with a source of a suitable base, for example potassium hydroxide, and a source of a suitable inorganic acid such as hydrochloric acid.

In addition to the carbon source, a source of nitrogen is required in the fermentation. The nitrogen source is generally organic in nature, for example peptone, distiller-dried solubles, or a concentrate of corn-solubles from the corn wet-milling process, preferably corn steep liquor. Corn steep liquor is the preferred nitrogen source for the production of NW-01. An amount ranging between 0.3–0.5 percent, preferably 0.4 percent, by weight of the fermentation medium is satisfactory.

Magnesium (0.01 percent by weight) and phosphorus (0.05 percent by weight) are also present in the fermentation medium. Suitable sources of magnesium ions include water soluble magnesium salts such as magnesium sulfate heptohydrate, magnesium chloride and magnesium acid phosphate. Phosphorus is usually added in the form of a soluble potassium salt.

It is essential to have a sufficient quantity of oxygen available for the fermentation. If either too much or too little oxygen is provided, the production of the heteropolysaccharide is slowed down. It has been found that a level of 40–50 percent of dissolved oxygen is required for the beginning 40–72 hours of the fermentation. Toward the end of the fermentation period, e.g. after about 96 hours, the level of dissolved oxygen does not seem critical.

On completion of the fermentation, the desired heteropolysaccharide may be recovered by first removing the cells by centrifugation or by enzymatic (protease) treatment. The fermentation beer is usually diluted to a viscosity range of 25–50 cps. The diluted broth is then centrifuged at 30,000 xg for about 30 minutes. The supernatant liquid is collected and 2% potassium chloride is added. The supernatant liquid is then mixed with 2 or 3 times its volume of a lower aliphatic alcohol to precipitate the heteropolysaccharide from the supernatant liquid. Suitable solvents to effect precipitation include isopropanol, acetone, methano, ethanol, n-butenol, secondary butenol, tertiary butenol, isobutenol and n-amyl alochol with isopropanol being preferred.

The composition of the heteropolysaccharide is determined by first dissolving one gram of the purified product in 100 ml of water. 100 ml of a 4N sulfuric acid is added to the resulting solution and the mixture incubated at 100° C. for three hours. The resulting solution is cooled and brought to pH 6.5–7.5 with barium hydroxide dihydrate. The resulting precipitated barium sulfate is separated by centrifugation. The supernatant is then frozen and then concentrated by lyophilization. The hydrolyzed heteropolysaccharide is analyzed by HPLC using an IBM-$NH_2$ column with acetonitrile water (79:21) solvent at a 1.5 cc/minute flow rate and ambient temperature. The sugars are identified by comparison with authentic standards to be glucose, arabinose and galactose.

EXAMPLE 1

The fermentation was carried out in a 7-liter fermentor. Flavobacterium sp. seed was prepared by inoculating 50 ml of CSL medium and transferring the culture to a Fernbach flask with 450 ml of CSL medium. The 500 ml inoculum was transferred into the fermentor. The fermentation temperature was 28° C. and the pH was controlled at 7. The dissolved oxygen level was maintained 40–50% for the first 72 hours and then at 10% until the end of the fermentation. The stirring speed was 400 rpm for the first 72 hours and 800 rpm for the rest of the fermentation. By 93 hours the viscosity of the beer was 7,000 cps and by 190 hours the viscosity was 15,600 cps. The beer was diluted, centrifuged at 30,000 xg to remove cells and 2% KCl was added to it. The heteropolysaccharide was precipitated by mixing the beer with twice the volume of isopropanol and recovered by straining it from the fermentation liquid. It was pressed to remove excess fluid and dried under reduced pressure. The heteropolysaccharide is obtained as a pale yellow-colored powder, (yield=1.58%).

In deionized water the heteropolysaccharide shows excellent viscosity/concentration relationship (Table 2). This demonstrates the superiority of the heteropolysaccharide as compared in general with other thickeners. In further tests 10 gms of the heteropolysaccharide was dissolved in 100 ml of deionized water using a Waring blender. The solution was diluted with deionized water to a final viscosity of 80, 120, and 180 cps. Sodium chloride was added to each tube so that the final concentration is 2%. Viscosity of each tube was measured. Additional salts are added so that the final concentration is 9% NaCl and 1% CaCl. The tubes are shaken vigorously and viscosities measured. The percent viscosity left after salt treatment at each concentration is shown in Table 3.

To determine the rapidity of viscosity recovery, a 0.5% solution was sheared in a Waring blender for 1 hour, the solution was permitted to stand, and the viscosity was measured at 0, 20, 40, and 60 minutes (Table 4).

A further experiment was performed to determine the shear sensitivity of the heteropolysaccharide. The viscosity of 0.5% (w/v) solution of the polysaccharide was measured at different shear rates and the results reported as in Table 5.

TABLE 2

| Conc. of heteropolysaccharide (ppm) | 0 | 250 | 500 | 750 | 1000 |
|---|---|---|---|---|---|
| viscosity (cps) | 1.5 | 6.4 | 21 | 38 | 63 |

TABLE 3

| Sample | 2% NaCl % viscosity left | 9% NaCl + 1% CaCl$_2$ % viscosity left |
|---|---|---|
| 80 cps | 50% | 45% |
| 120 cps | 67% | 33% |
| 180 cps | 60% | 44% |

TABLE 4

| time | viscosity (cps) | % original viscosity |
|---|---|---|
| 0 | 1,400 | 95 |
| 20 | 1,440 | 97 |
| 40 | 1,480 | 100 |
| 60 | 1,480 | 100 | viscosity of solution before blending = 1,480 cps

TABLE 5

| shear rate | viscosity (cps) |
|---|---|
| 18.42 | 354 |
| 12.30 | 473 |
| 6.42 | 734 |
| .21 | 9,295 |

I claim:

1. The compound Heteropolysaccharide-NW-01, said heteropolysaccharide consisting of glucose, arabinose and galactose in a 4.8:3.3:1 molar ratio and said heteropolysaccharide being soluble in water.

* * * * *